United States Patent [19]

Wong

[11] 4,081,448
[45] Mar. 28, 1978

[54] BRIDGEHEAD NITROGEN ANALOGS OF POLY-CHLORINATED CYCLIC HYDROCARBON INSECTICIDES

[75] Inventor: John Lui Wong, Louisville, Ky.

[73] Assignee: Research Corporation, New York, N.Y.

[21] Appl. No.: 672,322

[22] Filed: Mar. 31, 1976

Related U.S. Application Data

[63] Continuation-in-part of Ser. No. 454,576, Mar. 25, 1974, abandoned.

[51] Int. Cl.² .................. C07D 221/22; C07D 491/08
[52] U.S. Cl. .......................... 260/290 HL; 260/294.9; 260/295 T; 260/295.5 T; 260/297 T; 260/297 F; 424/256; 424/263
[58] Field of Search ..................... 260/290 HL, 297 F

[56] References Cited

U.S. PATENT DOCUMENTS 3,218,355  11/1965  Paulshock ........................ 260/297 T

*Primary Examiner*—Alan L. Rotman
*Attorney, Agent, or Firm*—Dennis P. Clarke

[57] ABSTRACT

A compound having one of the structural formulae:

a) 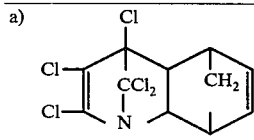 and hydrogenated, chlorinated and brominated derivatives thereof;

b)

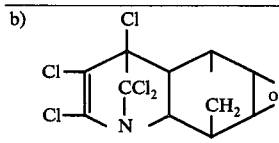

c)

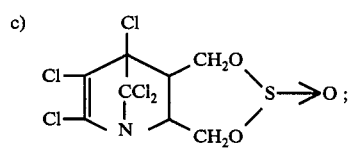

d) 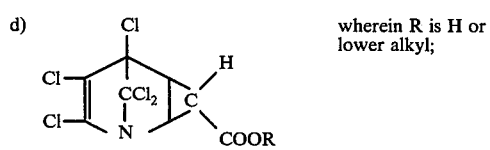 wherein R is H or lower alkyl;

e) 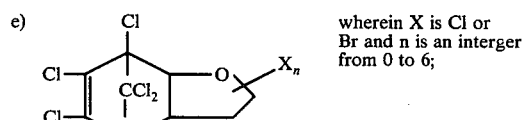 wherein X is Cl or Br and n is an interger from 0 to 6;

f) 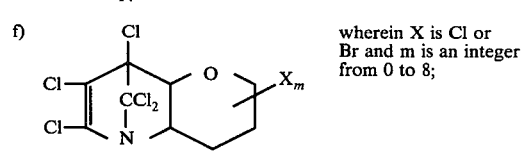 wherein X is Cl or Br and m is an integer from 0 to 8;

g) 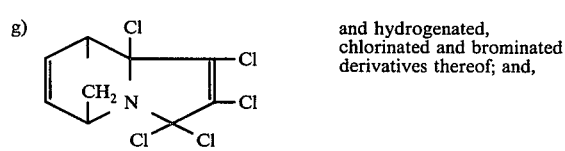 and hydrogenated, chlorinated and brominated derivatives thereof; and, h)

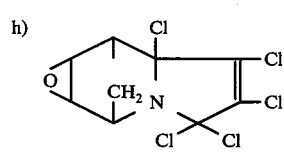

useful as insecticides.

3 Claims, No Drawings

BRIDGEHEAD NITROGEN ANALOGS OF POLY-CHLORINATED CYCLIC HYDROCARBON INSECTICIDES

RELATIONSHIP TO OTHER APPLICATIONS

This is a continuation-in-part application of application Ser. No. 454,576, filed Mar. 25, 1974, now abandoned.

BACKGROUND OF THE INVENTION

A well-known class of insecticides includes the polychlorinated cyclic hydrocarbons with endomethylene-bridged structures. These compounds are prepared by the well-known Diels-Alder [4 + 2] cyclo-addition reaction.

The tradenames of various of these insecticides are: Chlordane, Heptachlor, Heptachlor expoxide, Betadihydroheptachlor, Telodrin, Aldrin, Dieldrin, Endrin, Endosulfan (Thiodan), Aldodan, Mirex and Nonachlor.

These insecticides are conventionally used for the control of cockroaches, ants, termites and other household pets, soil insects and a variety of vegetable and field crop pests. They are good contact insecticides whose symptoms of poisoning include disturbance of the ganglia of the central nervous system upon absorption by the insect.

SUMMARY OF THE INVENTION

The present invention relates to a novel class of compounds possessing an activity similar to the polychlorinated cyclic hydrocarbons. The compounds of the invention are, in essence, the bridgehead nitrogen analogs of the above-mentioned commercial insecticides. They possess, generally, the same or better insecticidal properties, however, are advantageous in that they are more readily degraded after performing their function thereby lessening the deleterious impact on the environment.

The chlorinated polycyclic amines of the present invention are prepared by reacting pentachloro-α-pyrrolenine with norbornadiene, cyclopentadiene or other appropriate olefin in a Diels-Alder type cyclo-addition, followed by, in some instances- further treatment to yield a desired derivative.

DETAILED DESCRIPTION OF THE INVENTION

The compounds of the invention have the following structural formulae:

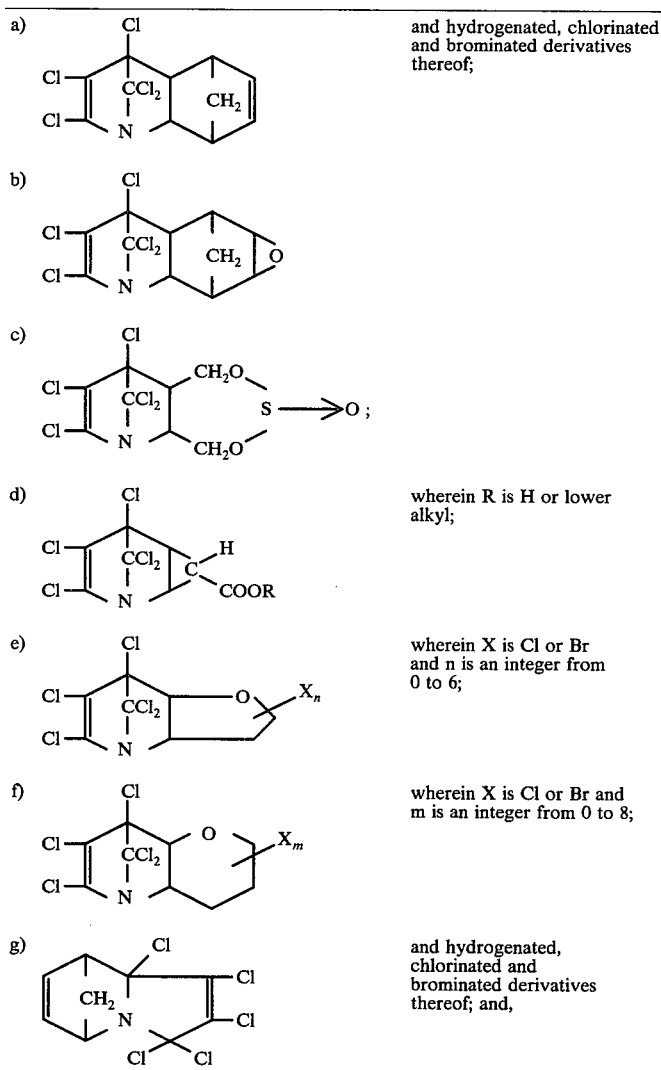

-continued h) 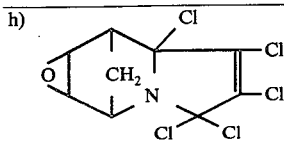

The reactions involved are exemplified by the following reaction schemes:

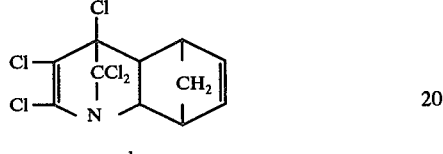

and

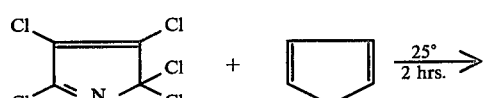

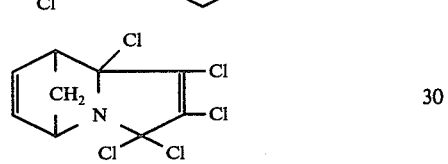

The chlorinated polycyclic amines of the invention are highly active insecticides. They are superior to the above-described chlorinated insecticides in that they are readily degradable whereas the chlorinated commercial insecticides are not. The latter have been found to be disadvantageous due to the accumulation of their residues in the environment posing a threat to the general health. As a consequence their use has been stringently regulated on both the Federal and state levels. Moreover, the pest colonies have developed widespread resistance to the above-described chlorinated hydrocarbon insecticides.

The polycyclic amines of the present invention lend themselves to relatively easy hydrolysis at the bridgehead nitrogen due to the presence of the N — CCl$_2$ moiety to an amino acid which may be biodegraded further. This degradation pathway is unavailable to the above-described commercial insecticides and is highly advantageous in that it solves the notorious residue problem associated therewith.

The presence of the bridgehead amino moiety also enhances the pharmacological effects of the insecticide on the nervous system of the insects. This enhancement of insecticidal efficiency reduces the problem of pest resistance considerably.

EXAMPLE 1

A mixture of 1 g (4.2 mmol) of pentachloro-α-pyrrolenine (Mazzara, Gazzetta Chemica Italiana, 32 II, 30, 1902) and 0.425 ml (4.2 mmol) of norbornadiene was placed in a sealed tube and heated at 80° C for 4 days. The reaction product was dissolved in 50% acetone-methanol and filtered through charcoal. The filtrate was evaporated and recrystallized five times from acetone-methanol yielding 1.10 g (80%) of 1-aza-2,3,4,10,10-pentachloro-1,4,4a,5,8,-hexahydro-1,4:5,8-dimethanonaphthalene, m.p. 97°-99° C. Anal. Calcd. for C$_{11}$H$_8$NCl$_5$:C,39.81; H,2,41; N,4.22. Found: C, 39.99; H,2.22; N,4.06.

The compound may be represented by the formula:

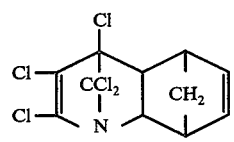

EXAMPLE 2

A mixture of 2 g (8.4 mmol) of pentachloro-α-pyrrolenine and 0.556 g (8.4 mmol) of cyclopentadiene was allowed to stand at room temperature overnight. The reaction mixture was dissolved in 50% aqueous ethanol and cooled. The precipitate was recovered and sublimed at 55° C, 0.1 mm to yield 1.9 g (74%) of product, m.p. 173°-174° C.

Anal. Calcd. for C$_9$H$_6$NCl$_5$; C, 35.35; H, 1.96; N, 4.58. Found: C, 35.36; H, 1.94; N, 4.46.

The compound may be represented by the formula:

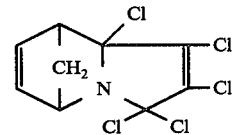

EXAMPLE 3

A mixture of 3.0 g (9.05 mmol) of the compound of Example 1 and 1.725 g (10 mmol) of m-chloroperbenzoic acid in 20 ml of chloroform was stirred at room temperature for 14 days. The reaction mixture was extracted successively with 3 × 3 ml of 5% aqueous sodium bisulfite solution and 3 × 3 ml of 5% aqueous solution bicarbonate solution. The organic layer was dried, evaporated, and the residue recrystallized three times from ether and sublimed at 60°/0.1 mm, yielding 2.3 g of 1-aza-2,3,4,10,10-pentachloro-6,7-epoxy-1,4,4a,5,6,7,8,8a-octahydro-1,4-endo-exo-5,8-dimethanonaphthalene. Anal. Calcd. for C$_{11}$H$_8$NOCl$_5$: C, 37.98; H, 2:30; N, 4.02. Found: C, 38.24; H, 2,21; N, 3.82.

The compound of Example 3 may be represented by the formula:

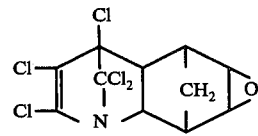

EXAMPLE 4

A mixture of 5.0 g (16.37 mmol) of the compound of Example 2 and 3.02 g (17.5 mmol) of m-chloroperbenzoic acid in 25 ml of chloroform was stirred at room temperature for 14 days. The reaction mixture was extracted successively with 3 × 3 ml of 5% aqueous sodium bisulfite solution and 3 × 3 ml of 5% aqueous sodium bicarbonate solution. The organic layer was dried, evaporated, and the residue recrystallized three times from ether, yielding 3.40 g of product.

Anal. Calcd. for $C_9H_6NOCl_5$: C, 33.59; H, 1.86; N, 4.35. Found: C, 33.79; H, 1.80; N, 3.99.

The compound of Example 4 may be represented by the formula:

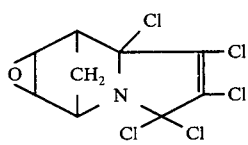

EXAMPLE 5

A mixture of 175 mg (0.574 mmol) of the compound of Example 2 and 92 mg (0.574 mmol) of bromine in 15 ml of methylene chloride was stirred at room temperature for 4 days. The solution was evaporated and the residue sublimed to yield 230 mg of product.

The compound may be represented by the formula:

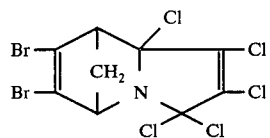

EXAMPLE 6

The compounds of Examples 1 and 2 were evaluated as mosquito larvicides and body louse toxicants according to the following methods.

BODY LOUSE TOXICANT

Compounds are screened as body louse (pediculus humanus humanus L.) toxicants by exposing young adult body lice on treated patches of woolen cloth, 3.8 cm in diameter. Duplicate patches are impaled on pinboards, and 0.7 ml of 1% solutions of the compounds in acetone or another volatile solvent is applied to them by pipette. After the patches are dried, 10 female lice are exposed to them in 50-ml glass beakers for 24 hours. Patches on which all lice are dead or knocked down are retested at intervals of 2 to 7 days until one or more lice remain unaffected. After 31 days the tests are terminated, even if the patches are still effective. DDT and malathion standards and an untreated patch are included for comparison. The standards are usually effective for more than 31 days under these conditions.

MOSQUITO LARVICIDES

Compounds are screened as mosquito larvicides by exposing early 4th-instar larvae of Anopheles quadrimaculatus Say to solutions or suspensions of the compounds in water (duplicate tests). The compounds are dissolved in acetone and added to water; water-soluble compounds remain in solution and the others become finely divided suspensions. Mosquito larvae are added to the treated water and mortality is determined after 24 hours of exposure. If 95% to 100% mortality occurs at the initial concentration of 10 parts per million, additional tests are made to determine the minimum effective concentration. Under these conditions, the LC 90 of the standard larvicide Abate[R], is 0.005 ppm.

As a residual louse toxicant, the compound of Example 1 remained 100% effective for >31 days whereas the compound of Example 2 was 100% effective for 17 days. In speed of action, the compound of Example 1 required 1 hour to produce 100% knockdown of lice exposed to the fresh treatment. The compound of Example 2 required >3 hours but <24 hours to produce 100% knockdown.

As mosquito larvicides, the compound of Example 1 produced mortalities of 100% and 96% at the 10 and 1 ppm concentrations, respectively. The compound was 20% effective at 0.1 ppm concentration.

EXAMPLE 7

The compounds of Examples 1 and 2 were compared with their commercial analogs, Aldrin and Chlordene as insecticides. The following test parameters were employed:

Host: cockroach ca. 1 g size. Vehicle: 95% ethanol. Mode of application: dropping ca. 50μl of solution onto roach back using a microsyringe. Blank: 95% ethanol.

The results are set forth below:

| Compound | Dosage (mol/g of host) | Observation | |
|---|---|---|---|
| | | Onset of nervous disorder after hr. | Death after, hr. |
| Aldrin | $3 \times 10^{-6}$ | 3 | 36 |
| Cmpd. of Ex. 1 | $3 \times 10^{-6}$ | 2 | 24 |
| Chlordene | $7 \times 10^{-6}$ | 24 | 48 |
| Cmpd. of Ex. 2 | $7 \times 10^{-6}$ | 1 | 36 |
| Blank | 75 μl | no effect | no effect |

The epoxidated compounds of Examples 3 and 4 may be prepared by reacting the starting material with any conventionally employed per-acid, e.g., peracetic acid, perbenzoic acid, per-chlorobenzoic acid, per-trifluorobenzoic acid, etc.

I claim:

1. A compound having a structural formula selected from the group consisting of:

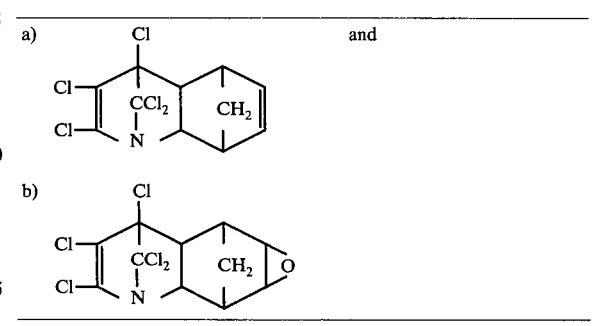

2. A compound of the formula:

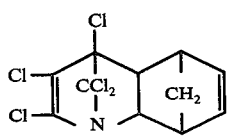
3. A compound of the formula:
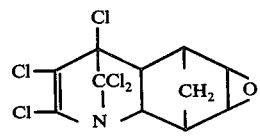
* * * * *